(12) United States Patent
Tegels (10) Patent No.: US 9,078,631 B2
(45) Date of Patent: Jul. 14, 2015

(54) DUAL HYPOTUBE SUTURE CUTTING DEVICE AND METHODS

(75) Inventor: Zachary J. Tegels, Otsego, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 550 days.

(21) Appl. No.: 12/839,813

(22) Filed: Jul. 20, 2010

(65) Prior Publication Data

US 2011/0029012 A1    Feb. 3, 2011

Related U.S. Application Data

(60) Provisional application No. 61/229,198, filed on Jul. 28, 2009.

(51) Int. Cl.
| | | |
|---|---|---|
| *A61B 17/08* | (2006.01) | |
| *A61B 17/00* | (2006.01) | |
| *A61B 17/04* | (2006.01) | |

(52) U.S. Cl.
CPC ......... *A61B 17/0057* (2013.01); *A61B 17/0467* (2013.01); *A61B 2017/00367* (2013.01); *A61B 2017/00615* (2013.01); *A61B 2017/00654* (2013.01); *A61B 2017/00659* (2013.01); *A61B 2017/0404* (2013.01); *A61B 2017/0414* (2013.01); *A61B 2017/0417* (2013.01); *A61B 2017/0464* (2013.01)

(58) Field of Classification Search
USPC ........................... 606/138, 148, 213, 232, 233
See application file for complete search history.

(56) References Cited

U.S. PATENT DOCUMENTS

| | | | |
|---|---|---|---|
| 6,045,569 A | 4/2000 | Kensey et al. | |
| 6,090,130 A | 7/2000 | Nash et al. | |
| 6,179,863 B1 | 1/2001 | Kensey et al. | |
| 7,618,436 B2 | 11/2009 | Forsberg | |
| 7,618,438 B2 | 11/2009 | White et al. | |
| 2005/0085851 A1 | 4/2005 | Fiehler et al. | |
| 2005/0192632 A1* | 9/2005 | Geissler et al. | 606/232 |
| 2006/0178682 A1* | 8/2006 | Boehlke | 606/148 |
| 2006/0293700 A1* | 12/2006 | Dana et al. | 606/148 |
| 2007/0005081 A1* | 1/2007 | Findlay et al. | 606/148 |
| 2007/0027476 A1* | 2/2007 | Harris et al. | 606/232 |
| 2007/0106310 A1* | 5/2007 | Goldin et al. | 606/148 |
| 2008/0228198 A1* | 9/2008 | Traynor et al. | 606/138 |
| 2009/0088780 A1* | 4/2009 | Shiono et al. | 606/148 |

* cited by examiner

*Primary Examiner* — Dianne Dornbusch
*Assistant Examiner* — Robert Lynch
(74) *Attorney, Agent, or Firm* — Holland & Hart (57) ABSTRACT

A tissue puncture closure device includes an anchor, a sealing pad, a compaction member, a suture, and a suture cutting member. The compaction member is configured to compress the sealing pad toward the anchor. The compaction member includes a sidewall and a first aperture defined in the sidewall. The suture cutting member is positioned in the compaction member and includes a suture cutting member sidewall and a second aperture defined in the suture cutting member sidewall. The suture is coupled to the sealing pad and anchor, and a portion of the suture extends through the first and second apertures. Relative movement between the compaction member and the suture cutting member severs the suture.

25 Claims, 11 Drawing Sheets

DUAL HYPOTUBE SUTURE CUTTING DEVICE AND METHODS

CROSS-REFERENCE TO RELATED APPLICATIONS

This application claims the benefit of U.S. Provisional Patent Application No. 61/229,198, filed Jul. 28, 2009, which is hereby incorporated by reference herein in its entirety.

TECHNICAL FIELD

The present disclosure relates generally to medical devices and more particularly to tissue puncture closure devices.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing tissue puncture closure devices, such as those described in U.S. Pat. Nos. 6,090,130 and 6,045,569, which are hereby incorporated in their entireties by this reference.

Prior closure devices, such as the ones described in the above-mentioned patents, place a sealing pad at the tissue puncture site. Deployment of the sealing pad involves ejecting the pad from within a device sheath and compacting the pad down to an outer surface of the tissue puncture using a compaction member. After the sealing pad has been compressed against the tissue puncture, the suture is manually cut by the operator at a location outside of the patient.

SUMMARY

One aspect of the present disclosure relates to a tissue puncture closure device that includes an anchor, a sealing pad, a compaction member, a suture, and a suture cutting member. The compaction member is configured to compress the sealing pad toward the anchor. The compaction member includes a sidewall and a first aperture defined in the sidewall. The suture cutting member is positioned in the compaction member and includes a suture cutting member sidewall and a second aperture defined in the suture cutting member sidewall. The suture is coupled to the sealing pad and anchor, and a portion of the suture extends through the first and second apertures. Relative movement between the compaction member and the suture cutting member severs the suture.

At least one of compaction member and the suture cutting member may define a cutting surface at the first and second apertures, respectively. The suture cutting member may be configured to cut the suture at a location within a percutaneous incision of a patient. One of the compaction member and the suture cutting member may include a channel feature extending axially from the first and second apertures, respectively. The compaction member may include a slot feature extending from the first aperture in a proximal direction. The suture cutting member may be rotatable relative to the compaction member to sever the suture.

At least one of the compaction member and the suture cutting member may include an overmold feature positioned between the compaction member and the suture cutting member. At least one of the compaction member and the suture cutting member may include a locking feature, wherein the locking feature is operable to releaseably connect the compaction member to the suture cutting member. At least one of the compaction member and the suture cutting member may include a circumferentially arranged channel feature configured to retain a wrapped portion of the suture.

Another aspect of the present disclosure relates to a suture cutting assembly adapted for use with a tissue puncture closure device. The suture cutting assembly includes a compaction member having a first aperture defined in a sidewall thereof, and a suture cutting member having a second apertures defined in a sidewall thereof. At least a portion of the suture cutting member is positioned in the compaction member. The first and second apertures are arranged to provide passage of a suture through the first and second apertures. Moving the suture cutting member relative to the compaction member cuts the suture.

Axially moving the suture cutting member in a first direction relative to the compaction member may apply a force to the suture to limit movement of the suture relative to the compaction member, and moving the suture in a second direction opposite the first direction cuts the suture. The first aperture may extend from a point proximal of a distal end of the compaction member to a proximal end of the compaction member. At least one of the compaction member and the suture cutting member may define a channel extending in a proximal direction from the first and second apertures, respectively. The first and second apertures may be at least partially radially aligned.

A further aspect of the present disclosure relates to a method of sealing a tissue puncture in an internal tissue wall that is accessible through a percutaneous incision. The method may include providing a tissue puncture closure device having an anchor, a sealing pad, a suture coupled to the anchor and the sealing pad, a compaction member, and a suture cutting device. The compaction member includes a first aperture defined in a sidewall thereof, the suture cutting member includes a second aperture defined in a sidewall thereof, and the suture extends through the first and second apertures. The method may also include inserting the tissue puncture closure device into the percutaneous incision, advancing the anchor through the tissue puncture, compressing the sealing member within the percutaneous incision, and moving the suture cutting device relative to the compaction member to cut the suture at a location within the percutaneous incision.

Moving the suture cutting device relative to the compaction member may include axially moving the suture cutting device relative to the compaction member. Moving the suture cutting device relative to the compaction tube may include rotating the suture cutting device relative to the compaction member. The method may also include positioning the suture in a channel defined between the compaction member and the suture cutting device. The method may further include maintaining tension in the suture by contacting the suture between a surface of the compaction member and a surface of the suture cutting device. The method still further may include providing at least one of the compaction member and the suture cutting device with an overmold feature that is positioned between the compaction member and the suture cutting device, wherein the overmold feature resists relative axial movement between the compaction member and the suture cutting device.

Additional advantages and novel features will be set forth in the description which follows or can be learned by those skilled in the art through reading these materials or practicing the examples disclosed herein.

BRIEF DESCRIPTION OF THE DRAWINGS

The accompanying drawings illustrate various embodiments of the present disclosure and are a part of the specification. The illustrated embodiments are merely examples and do not limit the scope of the invention.

Throughout the drawings, identical reference numbers designate similar, but not necessarily identical, elements.

DETAILED DESCRIPTION

As mentioned above, vascular procedures are conducted throughout the world and require access to a vessel through a puncture. Often, the vessel is a femoral artery. To close the puncture following completion of the procedure, many times a closure device is used to sandwich the puncture between an anchor and a sealing pad. A suture may be used to couple together the anchor and sealing pad. A force may be applied along the suture to draw the anchor and sealing pad toward each other as the sealing pad is compressed against the puncture. Typically, the suture is manually cut at a location outside of the patient after confirmation that the puncture has been sealed. Cutting the suture releases the anchor and sealing pad from the remaining portions of the closure device. A free end of the suture may extend from the patient's skin. Leaving a length of suture protruding through the patient's skin surface may result in complications such as, for example, infections that may arise where the suture exits the patient's skin. Further, requiring the extra step of manually cutting the suture with an instrument separate from the closure device requires additional time and complexity to the procedure.

The present disclosure describes methods and apparatus that facilitate cutting of the suture using features that are integral with the closure device. The present disclosure further describes methods and apparatus that facilitate cutting of the suture within a percutaneous incision at a location below the patient's outer skin surface. While the vascular instruments shown and described below include procedure sheaths and puncture sealing devices, the application of principles described herein are not limited to the specific devices shown. The principles described herein may be used with any medical device. Therefore, while the description below is directed primarily to arterial procedures and certain embodiments of a tissue puncture closure device, the methods and apparatus are only limited by the appended claims.

As used in this specification and the appended claims, the term "compact" or "compacting" is used broadly to mean any type of tamping (i.e., packing down by one or a succession of blows or taps or smooth, steady pressure, but not by excessive force), compacting, or compressing. "Engage" and "engagable" are also used broadly to mean interlock, mesh, or contact between two structures or devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

Referring to FIGS. 1-5, a tissue puncture closure device 100 is shown according to the prior art. Some example closure devices in addition to tissue puncture closure device 100 that may be suited for use with the inventive principles described herein are disclosed in U.S. Published Patent Application No. 2005/0085851 and U.S. Pat. Nos. 7,618,438 and 7,618,436, which applications are hereby incorporated in their entireties by this reference. The tissue puncture closure device 100 includes a carrier tube 102 with a filament or suture 104 extending at least partially therethrough. The tissue puncture closure device 100 also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the tissue puncture closure device 100 is properly placed and the anchor 108 deployed (see FIG. 4).

The carrier tube 102 typically includes a compaction member 112 disposed therein. The compaction member 112 is slidingly mounted on the suture 104 and may be used by an operator to compact the collagen pad 110 toward the anchor 108 at an appropriate time to seal a percutaneous tissue puncture.

Prior to deployment of the anchor 108 within a vessel, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 1:
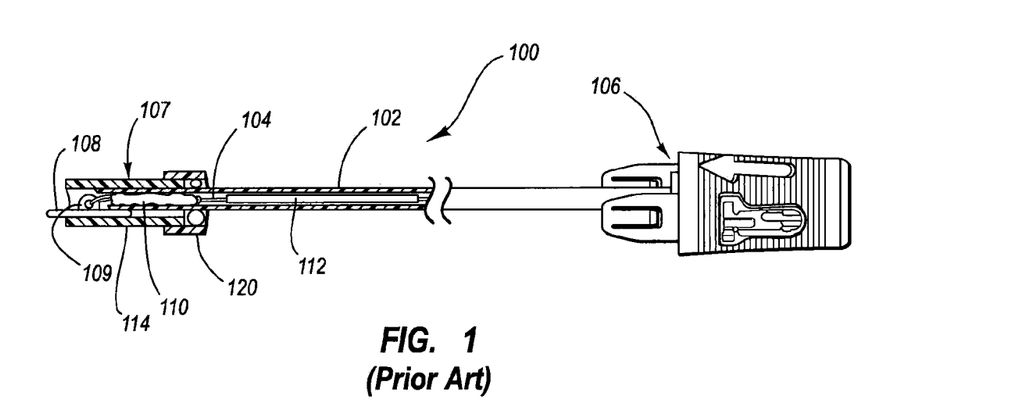
FIG. 1 is a side view of an example tissue puncture closure device according to the present disclosure.
Figure 2:
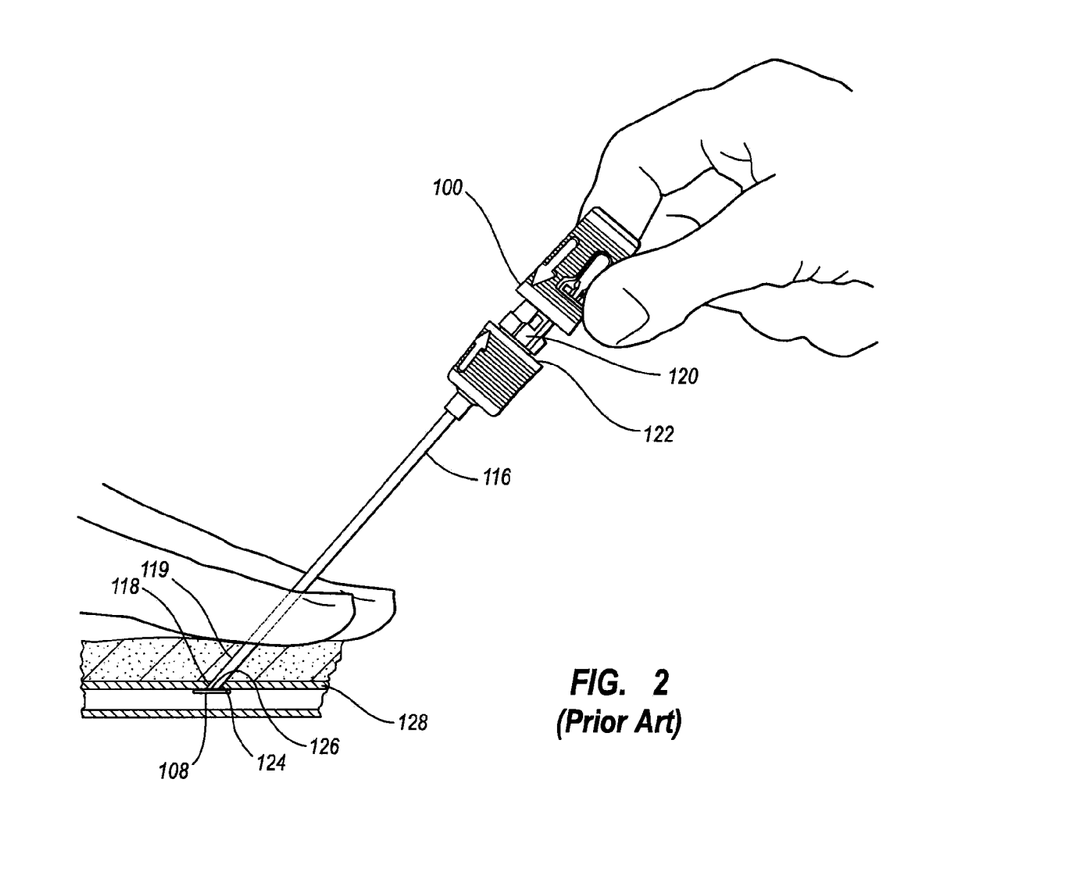
FIG. 2 is a side view of the tissue puncture closure device shown in FIG. 1 with an anchor disposed in a vessel.
Figure 3:
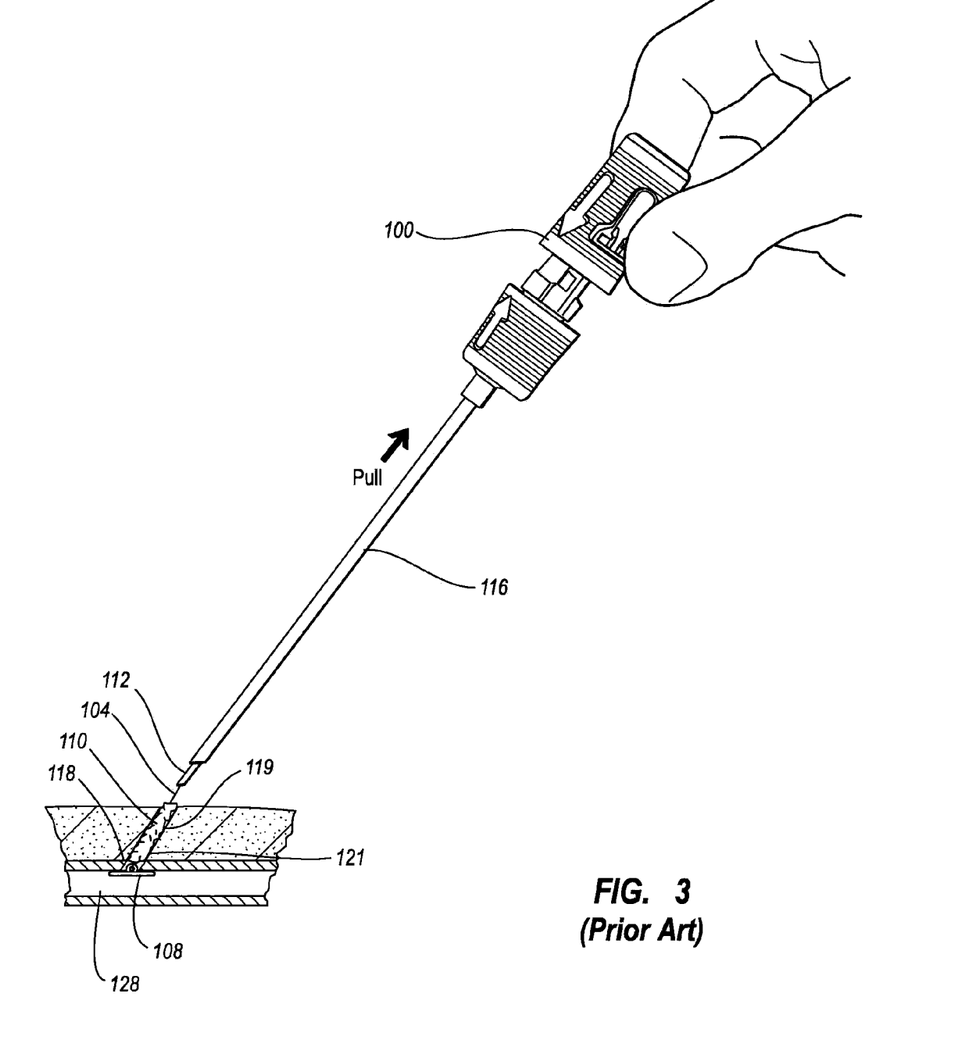
FIG. 3 is a side view of the tissue puncture closure device shown in FIG. 1. with the sealing pad disposed in the percutaneous incision.
Figure 4:
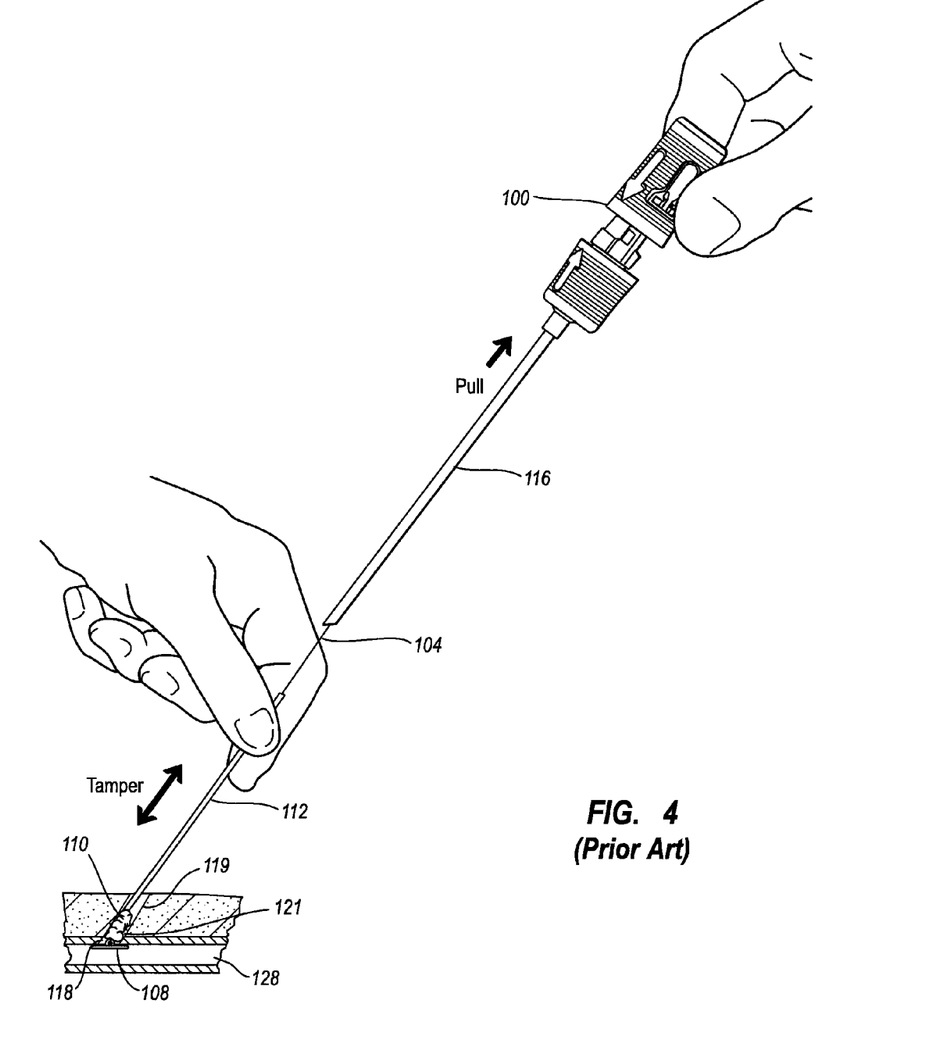
FIG. 4 is a side view of the tissue puncture closure device shown in FIG. 1 with the sealing pad being compacted with a compaction member.

The flush arrangement of the anchor 108 and carrier tube 102 allows the anchor 108 to be inserted into a procedure sheath such as insertion sheath 116 as shown in FIGS. 2-4, and eventually through an arterial puncture 118. The insertion sheath 116 is shown in FIGS. 2-4 inserted through a percutaneous incision 119 and into a vessel 128. However, the bypass tube 114 (see FIG. 1) includes an oversized head 120 that prevents the bypass tube 114 from passing through an internal passage of the insertion sheath 116. Therefore, as the tissue puncture closure device 100 is inserted into the insertion sheath 116, the oversized head 120 bears against a surface 122 of insertion sheath 116.

Further insertion of the tissue puncture closure device 100 results in sliding movement between the carrier tube 102 and the bypass tube 114, and releases the anchor 108 from the bypass tube 114 (see FIG. 1). However, the anchor 108 remains in the flush arrangement shown in FIG. 1 following release from the bypass tube 114, limited in movement by the insertion sheath 116.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the vessel 128, the anchor 108 is no longer constrained to the flush arrangement with respect to the carrier tube 102 and it deploys and rotates to the position shown in FIG. 2.

Referring next to FIGS. 3-4, with the anchor 108 deployed, the tissue puncture closure device 100 and the insertion sheath 116 are withdrawn together, ejecting the collagen pad 110 from the carrier tube 102 into the percutaneous incision 119 and exposing the compaction member 112. With the compaction member 112 fully exposed as shown in FIG. 4, the collagen pad 110 is manually compacted, and the anchor 108 and collagen pad 110 are cinched together and held in place with the self-tightening slip-knot on the suture 104. Thus, the tissue puncture is sandwiched between the anchor 108 and the collagen pad 110, thereby sealing the arterial puncture 118. The suture 104 is then cut and the percutaneous incision 119 may be closed. The suture 104, anchor 108, and collagen pad 110 are generally made of resorbable materials and therefore remain in place while the arterial puncture 118 heals.

It may be difficult to eject and compact the collagen pad 110 using the typical tissue puncture closure device 100 described above. The insertion sheath 116 resists deformation as the collagen pad 110 is ejected from the carrier tube and compacting cannot commence until the insertion sheath 116 has been removed so as to expose the compaction member 112 for manual grasping. Under certain conditions, removal of the insertion sheath 116 prior to compacting the collagen pad 110 causes the collagen pad 110 to retract or displace proximally from the arterial puncture 118, creating an undesirable gap 121 between the collagen pad 110 and the arterial puncture 118. The gap may remain even after compacting as shown in FIG. 4, and sometimes results in only a partial seal and bleeding from the arterial puncture 118.

Figure 5:
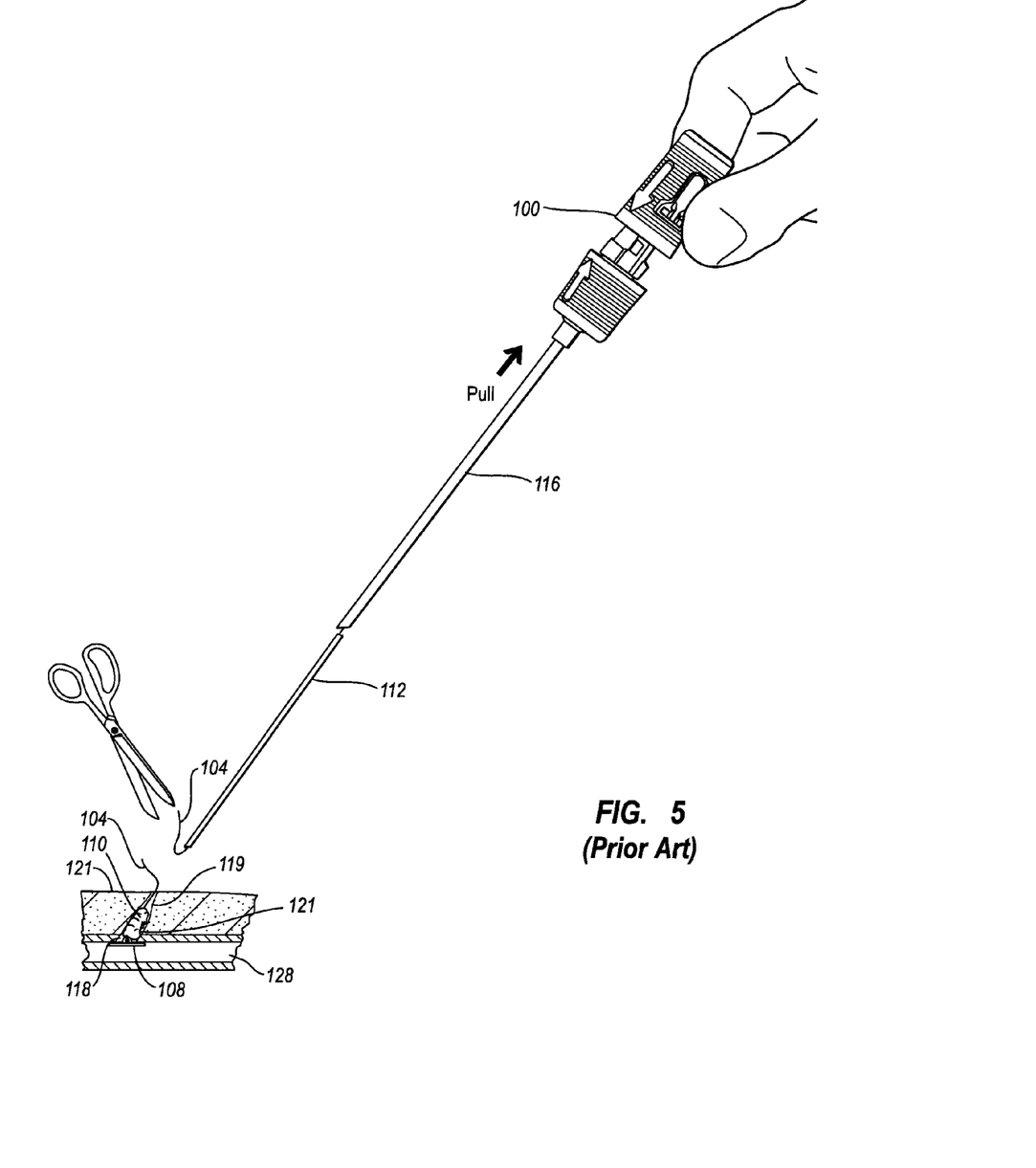
FIG. 5 is a side view of the tissue puncture closure device shown in FIG. 1 with the suture being cut at a location outside of the percutaneous incision.

FIG. 5 illustrates cutting of the suture 104 after compacting of the collagen pad 110 is completed. Typically, the suture 104 is cut using a cutting instrument 115 that is separate and distinct from the tissue puncture closure device 100. A free or cut end 105 of the suture 104 is located outside of the percutaneous incision 119. Thus, the suture 104 passes through an outer skin surface 121.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Figure 6:
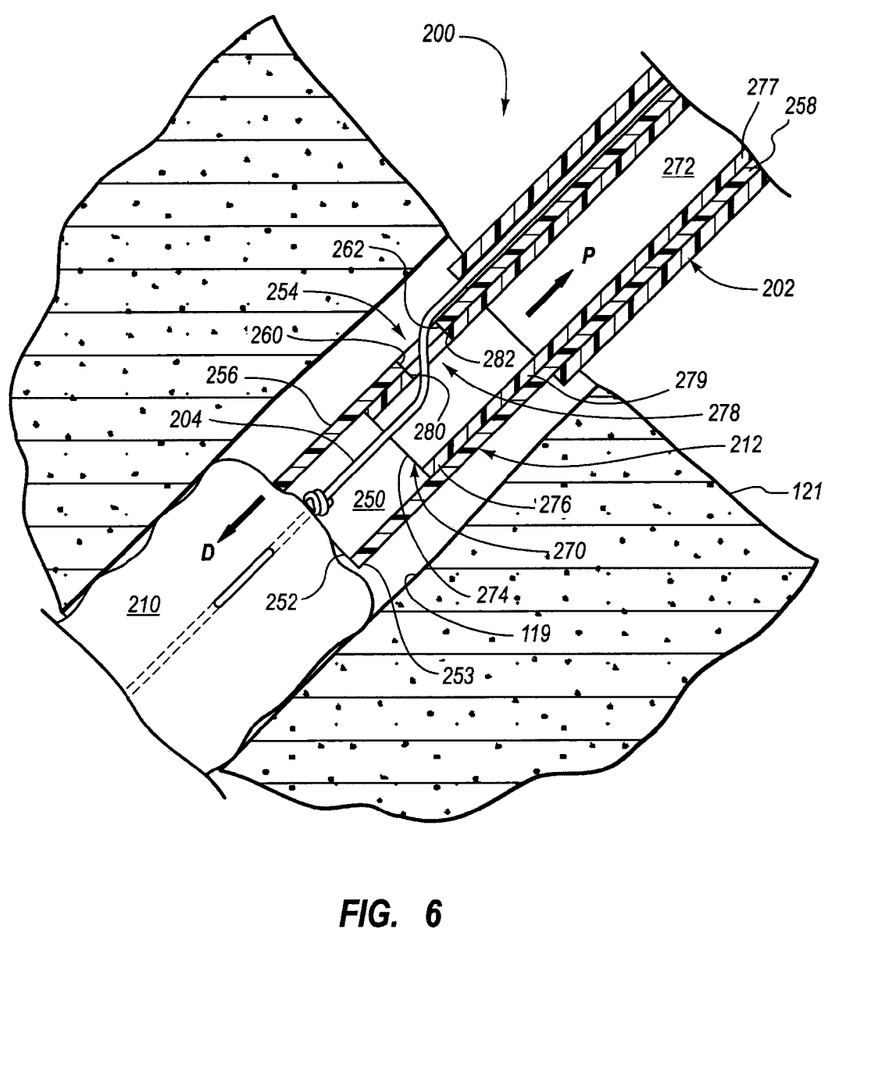
FIG. 6 is a cross-sectional side view of a portion of another example tissue puncture closure device disposed in a percutaneous incision.
Figure 7:
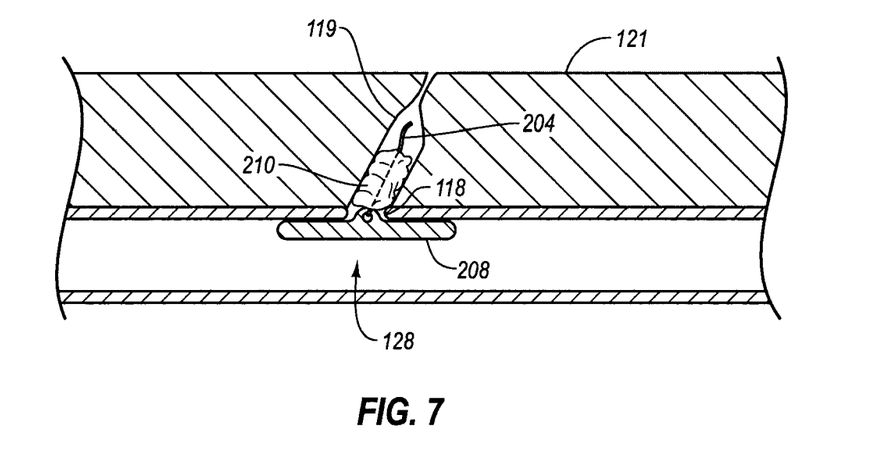
FIG. 7 is a side view of the tissue puncture closure device of FIG. 6 with the suture cut within the percutaneous incision.

Referring now to FIGS. 6 and 7, another example tissue puncture closure device 200 is shown and described. The tissue puncture closure device 200 includes a carrier tube 202, an anchor 208, a sealing pad 210, a compaction member 212, and a suture 204. The suture 204 is coupled to the anchor 208 and sealing pad 210. After compaction of the sealing pad 210 towards the anchor 208 with the compaction member 212, the suture 204 may be cinched against the sealing pad 210 to maintain the sealing pad 210 in a compacted state.

During the operation of the tissue puncture closure device 200, the anchor 208, sealing pad 210, suture 204, and compaction member 212 are all positioned within the carrier tube 202, such as the arrangement of similar components of tissue puncture closure device 100 shown in FIG. 1. Tissue puncture closure device 200 is inserted into the percutaneous incision 119 and the anchor 208 is advanced through the arterial puncture 118 into the vessel 128. The tissue puncture closure device 200 is retracted proximally until the anchor 208 engages against an inner surface of the vessel 128 adjacent to the arterial puncture 118. The carrier tube 202 is retracted to expose the sealing pad 210 within the percutaneous incision 119. In some arrangements, the compaction member 212 is then advanced distally in the direction D to compact the sealing pad 210 toward the anchor 208 into the compacted state shown in FIG. 7. As mentioned above, the suture 204 may be cinched against the sealing pad 210 to help maintain the sealing pad 210 in a compacted state and coupled to the anchor 208.

In at least some circumstances, it may be desirable to cut the suture 204 at a location within the percutaneous incision 119 and maintain a cut end of the suture 204 within the percutaneous incision 119. It may also be desirable to cut the suture 204 using features of the tissue puncture closure device 200 as opposed to an additional cutting device such as the scissors shown in FIG. 5, a scalpel, or other cutting device that the operator must handle separate from the tissue puncture closure device.

Tissue puncture closure device 200 may further include a suture cutter device 270, which alone or in combination with the compaction member 212, is capable of cutting the suture 204 within the percutaneous incision 119. In one arrangement, the suture cutter device 270 is sized and constructed to operate internal of the compaction member 212. The compaction member 212 may include a lumen or cavity 250, a distal end opening 252, a distal end portion 253, a first aperture 254, a side wall 256, and a proximal end portion 258. The distal end opening 252 is positioned at the distal end portion 253 and faces in a generally axial direction toward the sealing pad 210. The first aperture 254 is defined in the side wall 256 at a location spaced proximal of the distal end opening 252. The first aperture 254 may include a distal end 260 and a proximal end 262. A portion of the first aperture 254 may define a cutting surface. In at least one example, the distal end 260 defines a cutting surface configured to cut the suture 204. The lumen 250 may be sized to receive at least portions of the suture cutter device 270. In some arrangements, the lumen 250 may have a variable sized internal dimension along at least a portion of the length of the compaction member 212. The lumen 250 may also be sized to receive portions of the suture 204 for at least the distal end opening 252 to the first aperture 254.

A compaction member 212 may have a maximum outer dimension that is less than a minimum internal dimension of the carrier tube 202. A space defined between an outer surface of the compaction member 212 and the inner surface of the carrier tube 202 may be sized great enough to permit passage of the suture 204 therebetween along at least a portion of the length of the compaction member 212 proximal of the first aperture 254. In at least some arrangements, the suture 204 may extend proximally within the carrier tube 202 into a handle portion (not shown) in the tissue puncture closure device where an excess length of the suture is spooled or managed in other ways. The tissue puncture closure device 200 may apply tension to the suture 204 while compacting the sealing pad 210.

Figure 8:
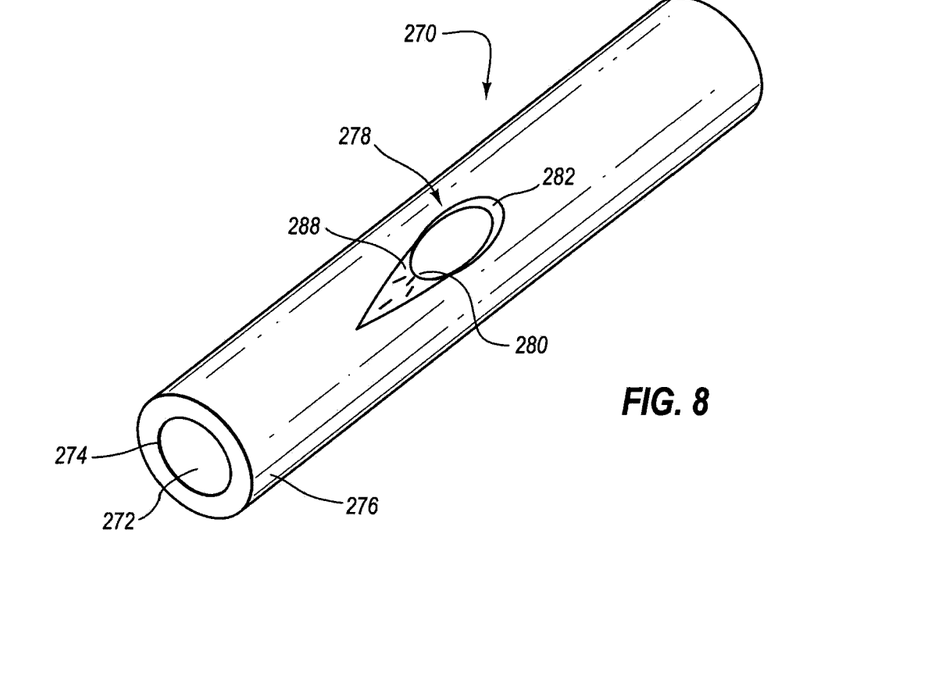
FIG. 8 is a perspective view of the example suture cutting device in accordance with the present disclosure.
Figure 9:
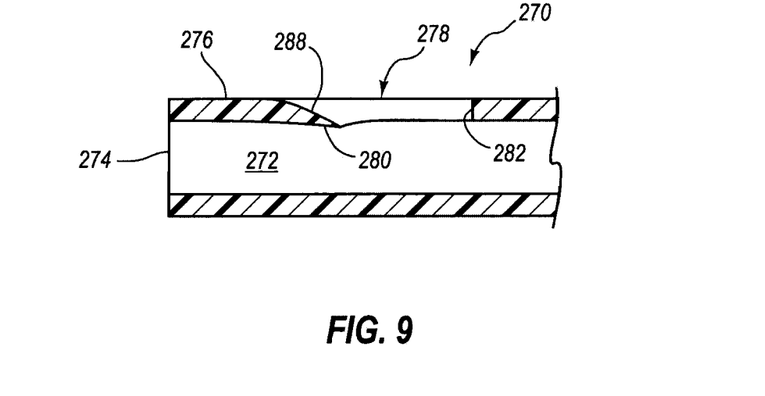
FIG. 9 is a partial cross-sectional side view of the suture cutting device of FIG. 8.

The suture cutter device 270 includes a lumen 272, a distal end opening 274, a distal end portion 276, a second aperture 278 and a proximal end portion 277 (see FIGS. 8 and 9). The distal end opening 274 is defined in the distal end portion 276 and faces in a generally axial direction towards the sealing pad 210. The second aperture 278 is defined in a side wall 279 of the suture cutter device 270 at a location proximal of the distal end opening 274. The lumen 272 is sized to receive the suture 204. The lumen 272 extends from at least the distal end opening 274 to the second aperture 278 to provide a pathway for the suture 204 to pass through the suture cutter device 270.

The second aperture 278 includes a distal end 280, a proximal end 282, and a cutting surface 288 (see FIGS. 8 and 9). The cutting surface 288 may be defined along any portion of the second aperture 278. In at least the embodiment shown in FIGS. 8 and 9, the cutting surface 288 is defined at the distal end 280. Referring to FIG. 9, the cutting surface 288 is shown having a pointed edge along the distal end 280 and the internal surface of the lumen 272. In other arrangements, the cutting surface may be defined along the exterior surface of the suture cutter device 270 along an edge of the second aperture 278. Many other shapes, sizes, and constructions for the second aperture 278 and the cutting surface associated with the second aperture are possible in other arrangements.

Referring again to FIG. 6, the first and second apertures, 254, 278 may be aligned radially and axially to provide a pathway for the suture 204 to travel from within the lumen 272 to a position outside of the compaction member 212. The path of the suture 204 extends from the anchor 208, through the sealing pad 210 into the distal end opening 252 of the compaction member 212, into the distal end opening 274 of the suture cutter device 270, through the second aperture 278, through the first aperture 254, and into the space defined between the inner surface of the carrier tube 202 and the outer surface of the compaction member 212.

The suture 204 may be cut by moving the compaction member 212 and suture cutter device 270 axially relative to each other. In one configuration in which the cutting surface 288 is positioned at the distal end 280 of the second aperture 278, moving the suture cutter device 270 in the proximal direction P relative to the compaction member 212 captures the suture 204 between the cutting surface 288 and the proximal end 262 of the first aperture 254, which results in cutting of the suture 204. In arrangements where cutting surfaces are defined along the distal or proximal end 260, 262 of the first aperture 254 or along the distal and proximal ends 280, 282 of the second aperture 278, relative axial movement (i.e., distal or proximal movement) between the compaction member 212 and suture cutter device 270 may result in cutting of the suture 204.

Relative axial movement between the compaction member 212 and suture cutter device 270 may be initiated at a location proximal of the skin surface 121 of the patient at, for example, the handle assembly of the tissue puncture closure device (not shown). In some arrangements, the compaction member 212 is held stationary while the suture cutter device 270 is moved axially. In other arrangements, the suture cutter device 279 is held stationary and the compaction member 212 is moved axially (i.e., in a distal direction D when compacting the sealing pad 210). It may be possible to move the compaction member 212 and suture cutter device 279 in opposite directions concurrently to cut the suture.

Figure 10:
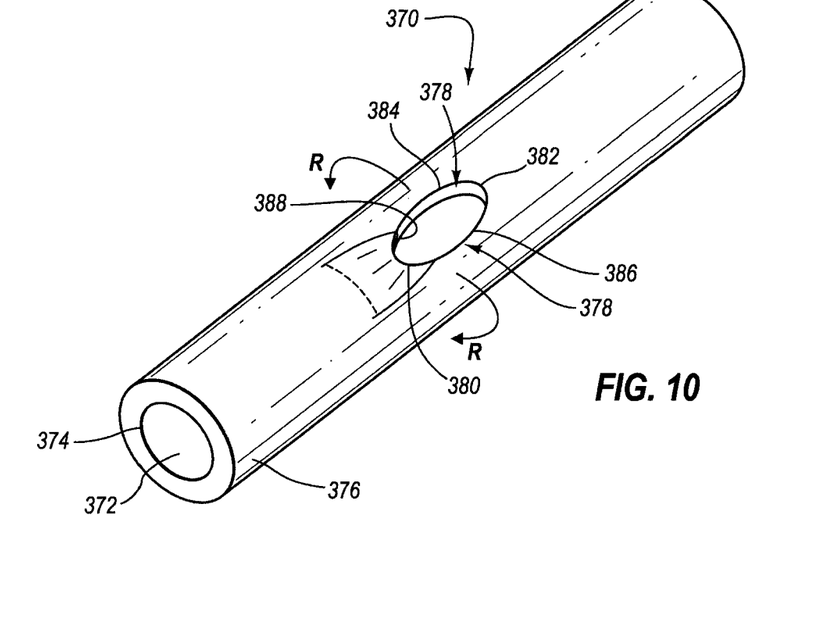
FIG. 10 is a perspective view of another example suture cutter device in accordance with the present disclosure.
Figure 11:
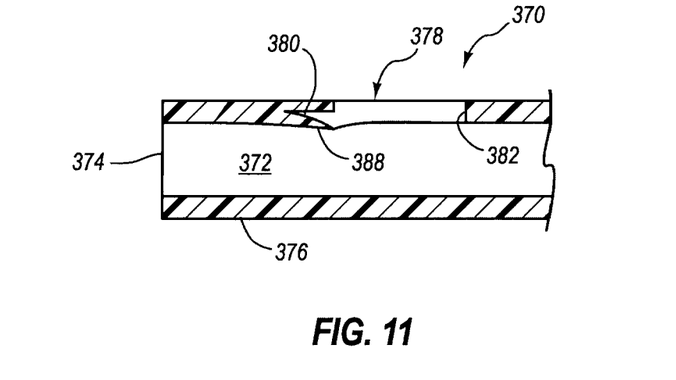
FIG. 11 is a partial cross-sectional side view of the suture cutter device of FIG. 10.

Referring now to FIGS. 10 and 11, another example suture cutter device 370 is shown and described. The suture cutter device 370 may include a lumen 372, a distal end opening 374, a distal end portion 376, and a second aperture 378 that includes distal and proximal ends 380, 382, first and second sides 384, 386, and a cutting surface 388. The cutting surface 388 extends around at least a portion of the second aperture 378 on at least one of the first and second sides 384, 386. The cutting surface 388 may be defined along other portions of the second aperture 378 such as along, for example, the proximal end 382, or along one or both of the first and second sides 384, 386.

The cutting surface 388 may be constructed to provide cutting of the suture 204, which is extending through the second aperture 378 and the first aperture 254, by rotation of the suture cutter device 370 relative to the compaction member in the direction R (see FIG. 10). The relative rotation between the suture cutter device 370 and the compaction member 212 may occur by maintaining the compaction member 212 in a fixed position while rotating the suture cutter device 270 in one of the directions R, or by maintaining the suture cutter device 370 in a fixed position while rotating the compaction member 212 in one of the rotation directions R. It may be possible to provide rotation of both of the compaction member 212 and suture cutter device 370 concurrently to cut the suture.

Figure 12:
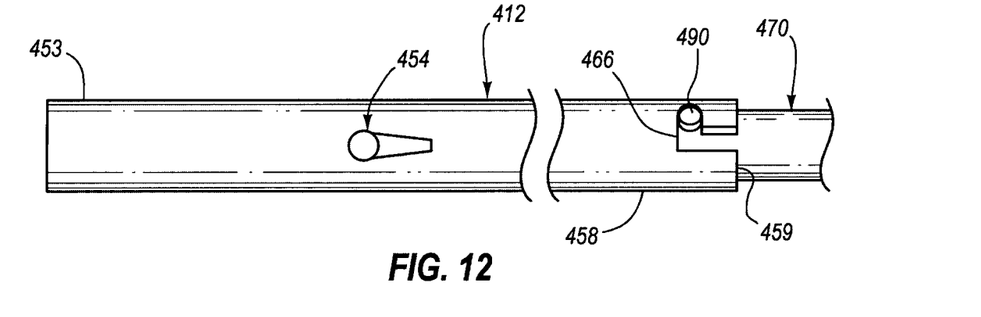
FIG. 12 is side view of an example suture cutter and compaction member assembly in accordance with the present disclosure.
Figure 13:
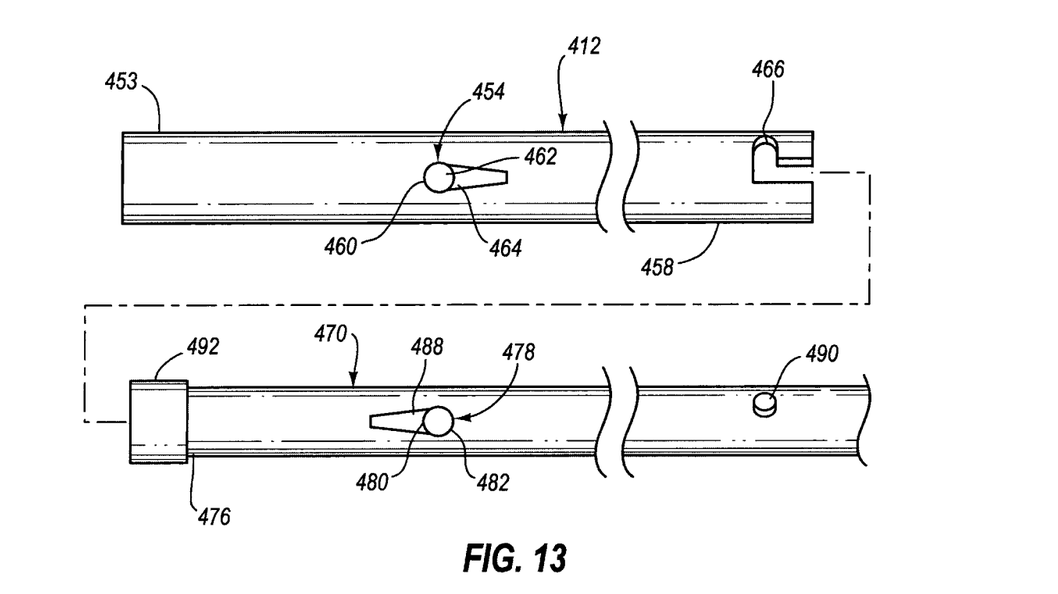
FIG. 13 is a exploded side view of the assembly of FIG. 12.

Referring now to FIGS. 12 and 13, another example suture cutter device 470 is shown and described with reference to another example compaction member 412. The compaction member 412 includes a lumen 450, a distal end portion 453, a first aperture 454 having distal and proximal ends 460, 462, a proximal end portion 458, a cutting surface 464, and a locking opening 466. The first aperture 454 is defined in the compaction member 412 at a location spaced between the distal and proximal end portions 453, 458. The cutting surface 464 is positioned along the proximal end 462 at the first aperture 454. In other arrangements, the cutting surface 464 may be positioned along other portions of the first aperture 454 such as, for example, along the proximal end 462 or along opposing sides of the first aperture 454.

The locking opening 466 (also referred to herein as a slot or locking slot) is positioned at the proximal end portion 458. In the illustrated example, the locking opening 466 is open along a proximal open end 459 of the compaction member 412. The locking opening 466 may include multiple sections that provide together relative locking between the compaction member 412 and the suture cutter device 470. In at least one arrangement, the locking opening 466 is configured to provide a fixed axial orientation between the compaction member 412 and suture cutter device 470 when in a locked state, and when in an unlocked state permit relative axial movement between the compaction member 412 and suture cutter device 470.

The suture cutter device 470 includes a distal end portion 476, a second aperture 478, a locking tab 490, and a first overmold 492. The second aperture 478 includes distal and proximal ends 480, 482, and a cutting surface 488 positioned along the distal end 480. In other arrangements, the cutting surface 488 may be positioned along the proximal end 482 or along portions of opposing sides of the second aperture 478.

The locking tab 490 may extend outward from an outer surface of the suture cutter device 470. The locking tab 490 may be configured to travel through the locking opening 466 of the compaction member 412. In at least one example, the locking tab 490 is a cylindrical shaped member having a circular cross section. Other shapes and constructions are possible for the locking tab 490. In some arrangements, the locking tab 490 and locking opening 466 are exchanged with each other so that the suture cutter device 470 includes a locking opening and the compaction member 412 includes a locking tab. The locking tab in such an arrangement may extend radially inward from an inner surface of the lumen 450 of the compaction member 412. Many other locking configurations are possible that provide at least some restriction to relative axial or rotational movement between the compaction member 412 and suture cutter device 470 when in a locked state, and permit relative axial or relative rotational movement between the compaction member 412 and suture cutter device 470 when in an unlocked state.

The first overmold 492 is positioned at the distal end portion 476 of the suture cutter device 470. The first overmold 492 may comprise a moldable material such as a polymer-based material (e.g., silicone or similar material). The first overmold 492 may be interposed between an outer surface of the suture cutter device 470 and an inner surface along the lumen 450 of the compaction member 412. The first overmold 492 may provide some frictional contact between the compaction member 412 and suture cutter device 470 that limits unintentional axial or rotational movement between the compaction member 412 and suture cutter device 470. The first overmold 492 may be positioned at any location along the length of the suture cutter device 470. In some arrangements, multiple overmolds are positioned at axially spaced apart locations along the length of the suture cutter device 470. In other arrangements, the overmold may be divided into separate segments spaced around a circumference of the suture cutter device 470. In still further arrangements, the first overmold 492 may be mounted to an interior surface of the compaction member 412 within the lumen 450.

The arrangement of cutting surfaces 464, 488 provides cutting of a suture that extends through the first and second apertures 454, 478 when the suture cutter device 470 moves in a proximal direction relative to the compaction member 412. Movement of the suture cutter device 470 in the distal direction relative to the compaction member 412 may bind the suture between the distal end 460 and proximal end 482 of the first and second apertures 454, 478 to retain the suture in a fixed position. Such binding of the suture may also permit creation of tension in the suture during, for example, delivering the sealing pad into a percutaneous incision and compacting the sealing pad.

Figure 14:
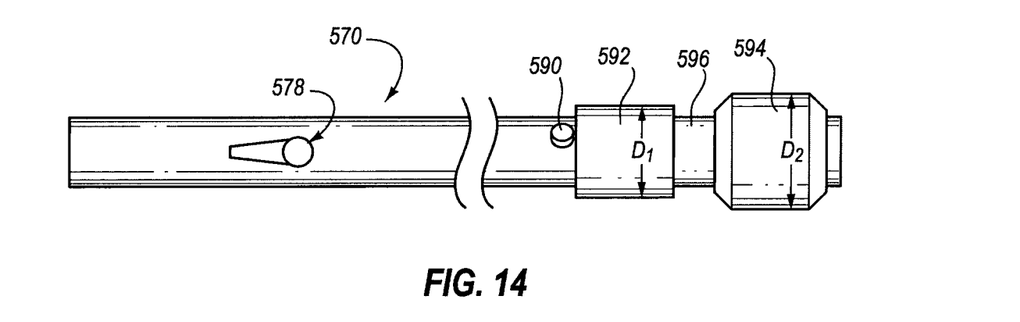
FIG. 14 is a side view of another example suture cutter device and compaction member assembly in accordance with the present disclosure.

Referring now to FIG. 14, another example suture cutter device 570 is shown and described. The suture cutter device 570 may be configured for use with the compaction member 412 described above as referenced to FIGS. 12 and 13. The suture cutter device 570 includes a second aperture 578, a locking tab 590, a first overmold 592, a second overmold 594, and a suture retention area 596. The first and second overmolds 592, 594 may be spaced apart axially to define the suture retention area 596. In some arrangements, the suture retention area 596 may be defined in one or both of the first and second overmolds 592, 594 The suture retention area 596 may be configured to provide a space within which a length of suture may be wrapped. In some arrangements, a suture retention area may be provided on a portion of the compaction member 412.

The first overmold 592 has a maximum outer dimension or diameter D1. Typically, the dimension D1 is no greater than a minimum internal dimension of the lumen 450 of the compaction member 412. The first overmold 592 may provide some resistance to unintentional axial or rotational movement between the suture cutter device 570 and the compaction member 412 when the suture cutter device 570 is inserted into the compaction member 412 (i.e., when the first aperture 454 is aligned with the second aperture 578). In some arrangements, the second overmold 594 may have a maximum outer dimension or diameter D2. The diameter D2 may be greater than diameter D1.

Figures 15, 16:
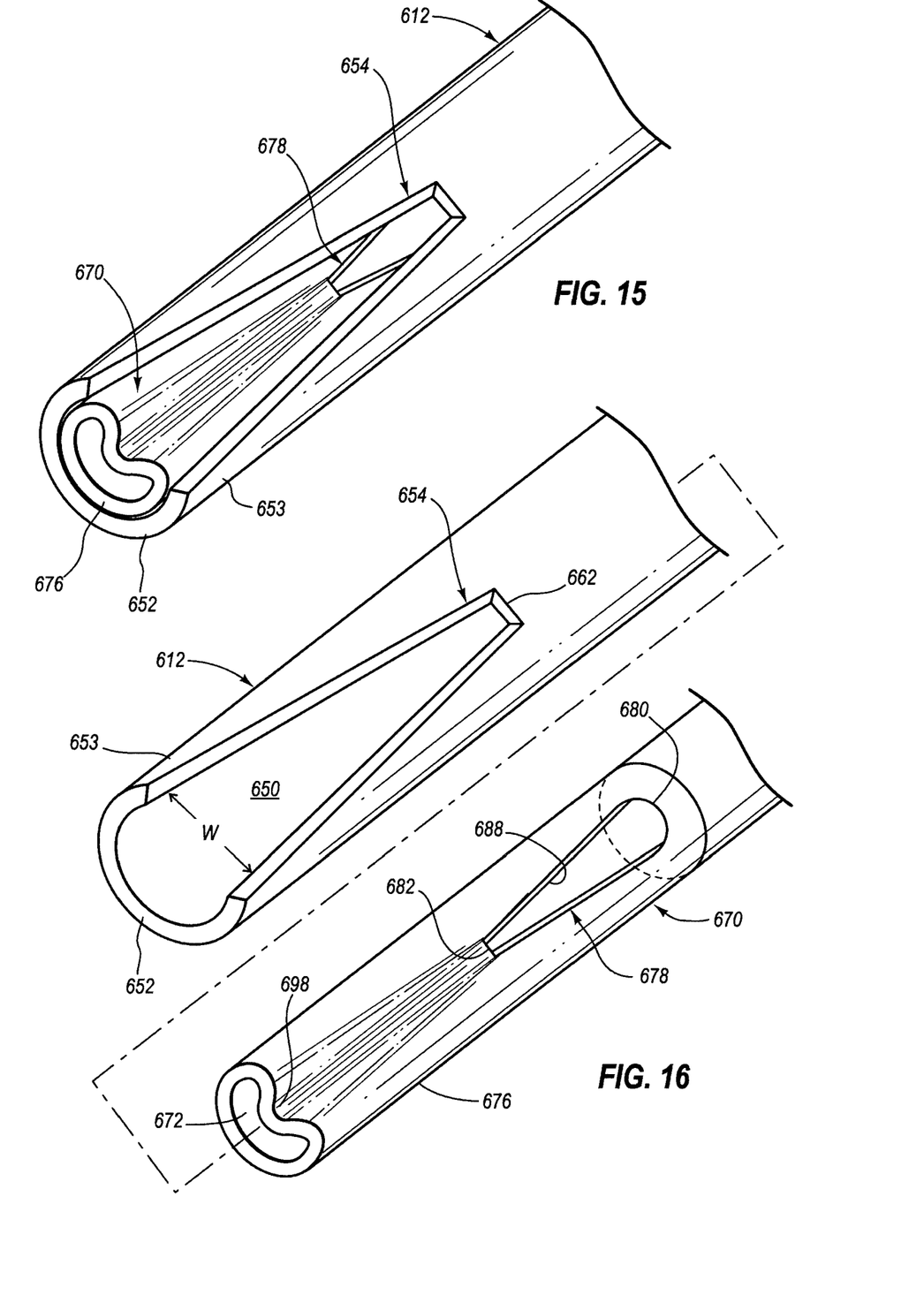
FIG. 15 is a perspective view of another example suture cutter device and compaction member assembly in accordance with the present disclosure.
FIG. 16 is a exploded perspective view of the assembly of FIG. 15.

Referring now to FIGS. 15 and 16, another example arrangement of a compaction member 612 and a suture cutter device 670 is shown and described. The compaction member 612 may include a lumen 650, a distal end portion 653, and a first aperture 654 having distal and proximal ends 660, 662. The first aperture 654 may extend from a distal open end 652 in a proximal direction to the proximal end 662. The first aperture 654 may have a variable width W that increases in size moving from the proximal end 662 to the distal end 660. In at least one arrangement, portions of the first aperture 654 may define a cutting surface. The first aperture 654 may have different constructions in alternative embodiments. For example, the width W of the first aperture 654 may be relatively constant along its length. In another example, the proximal end 662 may have a curve or contoured construction rather than the generally linear construction shown in FIGS. 15 and 16.

The suture cutter device 670 includes a lumen 672, a distal end portion 676, and a second aperture 678. The second aperture 678 may include a distal end 680, a proximal end 682, and a cutting surface 688. The cutting surface 688 may extend along opposing sides of the second aperture 678 at locations between the distal and proximal ends 680, 682. In other arrangements, the cutting surface 688 may be defined along at least portions of the distal and proximal ends 680, 682.

The suture cutter device 670 may also include a channel feature 698 that extends along at least a portion of a length of the suture cutter device 670. The channel 698 may be defined by a crescent cross-sectional shape that is formed in the suture cutter device 670 along at least a portion of its length. In the illustrated example, the crescent cross-sectional shape is defined at the distal end portion 676 and terminates at the second aperture 678. Other constructions are possible for defining the channel 698. In at least one example, the channel 698 is defined using a swaging, stamping or extruding techniques.

The channel 698 may be sized to retain a suture therein so that the suture may be positioned between an outer surface of the suture cutter device 670 and an internal surface of the compaction member 612 along the lumen 650. The suture may extend within the channel 698 from the distal end portion 653 and then pass through the second aperture 678 into the lumen 672. The sutures may extend proximally from the second aperture 678 to a location where the proximal end portion of the suture may be handled by another feature of the tissue puncture closure device or by the operator. With the suture extending from the channel 698 into the second aperture 678, movement of the suture cutter device 670 in the proximal direction relative to the compaction member 612 will capture the suture between the cutting surfaces 688 and the proximal end 662 of the compaction member 612, thereby cutting the suture.

Channel features such as the channel 698 may be defined in other portions of the suture cutter device or within portions of the compaction member. In at least one example, a channel is defined along an exterior surface of the compaction member. In another example, the channel is defined along an interior surface along an internal lumen of the compaction member. It a still further arrangement, the channel is defined in an outer surface of the suture cutter device in an arrangement wherein the channel is not exposed within a first aperture of the compaction member as in the embodiment illustrated in FIGS. 15 and 16. As described above, the channel feature, whether defined in one or both of the compaction member and suture cutter device, may be defined by any desired technique, such as, for example, swaging, extruding, stamping, or heat forming. The channel feature may extend along a portion or an entire length of either one of the compaction member and suture cutter device.

Figure 17:
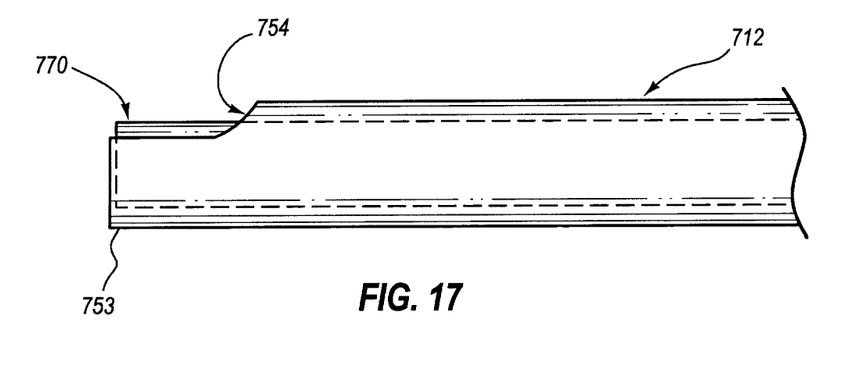
FIG. 17 is a side view of another example suture cutter device and compaction member assembly in accordance with the present disclosure.
Figure 18:
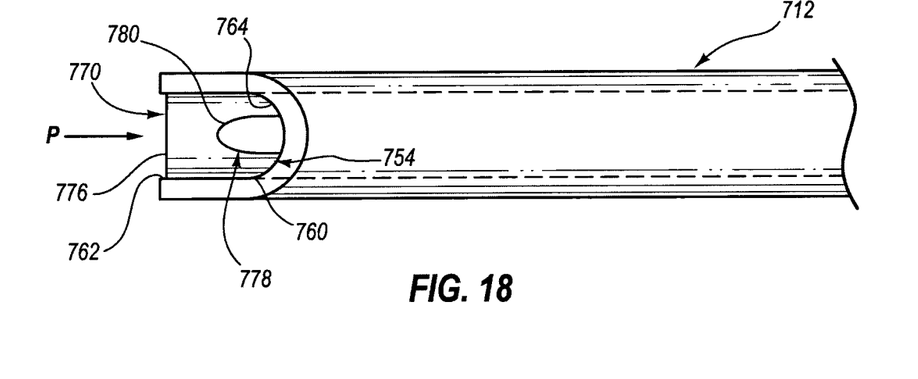
FIG. 18 is a top view of the assembly of FIG. 17.

Referring now to FIGS. 17 and 18, another example arrangement of a compaction member 712 and a suture cutter device 770 are shown and described. The compaction member 712 includes a distal end portion 753, a first aperture 754 having distal and proximal ends 760, 762, and a cutting surface 764. The act of forming the first aperture 754 may define the cutting surface 764 along the proximal end 762. In some arrangements, the cutting surface 764 is formed in a separate step from forming the remaining portions of first aperture 754. The distal end 760 of the first aperture 754 may extend to a distal end of the compaction member 712 to, for example, improve ease of manufacturing or to provide sufficient space for a suture to pass along an exterior surface of the suture cutter device 770 and into a second aperture 778 of the suture cutter device.

The suture cutter device 770 may include a distal end portion 776, a second aperture 778, and a distal end 780. The second aperture 778 may have any shape, size and construction, including, for example, a cutting surface along at least a portion of the second aperture 778. As noted above, the arrangement of the first and second apertures 754, 778 may provide for a pathway for the suture to pass along an exterior surface of the suture cutter device 770 and through the second aperture 778 into an internal lumen of the suture cutter device 770, or along an internal lumen of the suture cutter device from a distal end of the suture cutter device and out through the second aperture 778 and first aperture 754. In either one of these suture arrangements, proximal movement of the suture cutter device 770 relative to the compaction member 712 will capture the suture between the cutting surface 764 and the distal end 780 of the second aperture 778 to provide cutting of the suture.

In other arrangements, an aperture construction similar to first aperture 754 may be defined in the distal end portion of the suture cutter device 770 and an aperture of similar construction to the second aperture 778 may be defined in the compaction member 712 (i.e., reversal of the first and second apertures 754, 778). In this arrangement, the cutting surface may be defined along the aperture of the suture cutting device and cutting occurs by the suture cutter device moving in a distal direction relative to the compaction member 712. Many other arrangements and constructions for the first and second apertures and the cutting surfaces associated with those apertures are possible.

The first and second apertures 754, 778 may be formed using a variety of techniques such as, for example, laser cutting, machining, or electric discharge machining (EDM). These techniques may be especially useful when the compaction member and suture cutter device comprise a metal material, such as stainless steel. In all of the examples described herein, at least one of the compaction member and suture cutter device may comprise a metal material. In other examples, at least one of the compaction member and suture cutter device may comprise a polymer-based, rubber, ceramic, composite, or other type of material. Forming the apertures and cutting surfaces in the compaction members and suture cutter devices disclosed herein may be conducted using many different techniques, such as those described above relating to the various examples shown in FIGS. 6-18. Further, any of those features described with reference to the examples shown in FIGS. 6-18 may be used interchangeably with each other.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:
1. A tissue puncture closure device, comprising:
 a carrier tube;
 an anchor;
 a sealing pad positioned within the carrier tube during delivery to a tissue puncture;
 a compaction member positioned in and movable axially relative to the carrier tube to compress the sealing pad toward the anchor after the sealing pad is disposed at the tissue puncture, the compaction member including a sidewall and a first aperture defined in the sidewall;
 a suture cutting member positioned in the compaction member, the suture cutting member including a suture cutting member sidewall and a second aperture defined in the suture cutting member sidewall;
 a suture coupled to the sealing pad and anchor, a portion of the suture extending through the first and second apertures;
 a channel feature formed axially along an outer surface of the suture cutting member, the channel feature being positioned to receive the suture extending within the channel feature along the compaction member and external to the outer surface of the suture cutting member;
 wherein relative movement between the compaction member and the suture cutting member severs the suture.

2. The tissue puncture closure device of claim 1, wherein at least one of the compaction member and the suture cutting member defines a cutting surface at the first and second apertures, respectively.

3. The tissue puncture closure device of claim 1, wherein the suture cutting member is configured to cut the suture at a location within a percutaneous incision of a patient.

4. The tissue puncture closure device of claim 1, wherein the channel feature extends axially from at least one of the first and second apertures.

5. The tissue puncture closure device of claim 1, wherein the compaction member includes a slot feature extending from the first aperture in a proximal direction.

6. The tissue puncture closure device of claim 1, wherein the suture cutting member is rotatable relative to the compaction member to sever the suture.

7. The tissue puncture closure device of claim 1, wherein at least one of the compaction member and the suture cutting member includes an overmold feature positioned between the compaction member and the suture cutting member.

8. The tissue puncture closure device of claim 1, wherein at least one of the compaction member and the suture cutting member includes a locking feature, the locking feature being operable to releasably connect the compaction member to the suture cutting member.

9. The tissue puncture closure device of claim 1, wherein at least one of the compaction member and the suture cutting member includes a circumferentially arranged channel feature configured to retain a wrapped portion of the suture.

10. The tissue puncture closure device of claim 1, wherein the suture extends within the carrier tube proximal of the first and second apertures.

11. A suture cutting assembly adapted for use with a tissue puncture closure device having a carrier tube, an anchor, and a sealing pad, comprising:
a compaction member having a first aperture defined in a sidewall thereof and extending to a distal end surface of the compaction member, the compaction member being configured to be positioned in and movable axially relative to the carrier tube to compress the sealing pad toward the anchor;
a suture cutting member having a second aperture defined in a sidewall thereof, at least a portion of the suture cutting member being positioned in the compaction member, wherein the first and second apertures are arranged to provide passage of a suture through the first and second apertures;
a channel feature formed axially along an outer surface of the suture cutting member, the channel feature being positioned to receive the suture extending within the channel feature along the compaction member and external to the outer surface of the suture cutting member;
wherein concurrently moving the suture cutting member and the compaction member in opposite axial directions cuts the suture.

12. The suture cutting assembly of claim 11, wherein axially moving the suture cutting member in a first direction relative to the compaction member applies a force to the suture to limit movement of the suture relative to the compaction member, and moving the suture in a second direction opposite the first direction cuts the suture.

13. The suture cutting assembly of claim 11, wherein the first aperture is tapered from a point proximal of a distal end of the compaction member to the distal end surface of the compaction member.

14. The suture cutting assembly of claim 11, wherein the channel feature extends in a distal direction from at least one of the first and second apertures.

15. The suture cutting assembly of claim 11, wherein the first and second apertures are at least partially radially aligned.

16. The suture cutting assembly of claim 11, wherein the suture extends within the carrier tube proximal of the first and second apertures.

17. A suture cutting assembly adapted for use with a tissue puncture closure device having an anchor and a sealing pad, comprising:
a carrier tube;
a compaction member positioned in and movable axially relative to the carrier tube to compress the sealing pad toward the anchor, the compaction member having a first aperture defined in a sidewall thereof, the first aperture having an oval shape;
a suture cutting member having a second aperture defined in a sidewall thereof, the second aperture having an oval shape with a distal end and a proximal end, the distal end including a cutting surface, at least a portion of the suture cutting member being positioned in the compaction member, wherein the first and second apertures are arranged to provide passage of a suture through the first and second apertures;
a channel feature formed axially along an outer surface of the suture cutting member, the channel feature being positioned to receive the suture extending within the channel feature along the compaction member and external to the outer surface of the suture cutting member;
wherein moving the suture cutting member proximally relative to the compaction member cuts the suture.

18. The suture cutting assembly of claim 17, wherein axially moving the suture cutting member in a distal direction relative to the compaction member applies a force to the suture to limit movement of the suture relative to the compaction member.

19. The suture cutting assembly of claim 17, wherein a sidewall of the suture cutting member at the distal end of the second aperture has a tapered thickness.

20. The suture cutting assembly of claim 17, wherein the suture extends within the carrier tube proximal of the first and second apertures.

21. A suture cutting assembly adapted for use with a tissue puncture closure device having an anchor and a sealing pad, comprising:
a carrier tube;
a compaction member positioned in and movable axially relative to the carrier tube to compress the sealing pad toward the anchor, the compaction member having a first aperture defined in a sidewall thereof, the first aperture having a circular shape;
a suture cutting member having a second aperture defined in a sidewall thereof, the second aperture having a circular shape at least a portion of the suture cutting member being positioned in the compaction member, at least one of the first and second apertures having a cutting surface;
wherein the first and second apertures are arranged to provide passage of a suture through the first and second apertures;
a channel feature formed axially along an outer surface of the suture cutting member, the channel feature being positioned to receive the suture extending within the channel feature along the compaction member and external to the outer surface of the suture cutting member;

wherein moving the suture cutting member axially relative to the compaction member cuts the suture.

22. The suture cutting assembly of claim 21, wherein axially moving the suture cutting member in a distal direction relative to the compaction member applies a force to the suture to limit movement of the suture relative to the compaction member, and axially moving the suture cutting member in a proximal direction relative to the compaction member cuts the suture.

23. The suture cutting assembly of claim 21, wherein a sidewall of the suture cutting member adjacent to a portion of the second aperture has a tapered thickness.

24. The suture cutting assembly of claim 21, wherein a sidewall of the compaction member adjacent to a portion of the first aperture has a tapered thickness.

25. The suture cutting assembly of claim 21, wherein the suture extends within the carrier tube proximal of the first and second apertures.

\* \* \* \* \*